United States Patent
Arnett

(10) Patent No.: US 6,506,217 B1
(45) Date of Patent: Jan. 14, 2003

(54) MOLDABLE POST-IMPLANTATION BONE FILLER AND METHOD

(75) Inventor: G. William Arnett, Santa Barbara, CA (US)

(73) Assignee: Arnett Facial Reconstruction Courses, Inc., Santa Barbara, CA (US)

(*) Notice: Subject to any disclaimer, the term of this patent is extended or adjusted under 35 U.S.C. 154(b) by 0 days.

(21) Appl. No.: 09/537,281

(22) Filed: Mar. 28, 2000

Related U.S. Application Data

(60) Provisional application No. 60/126,745, filed on Mar. 29, 1999.

(51) Int. Cl.$^7$ .................................................. A61F 2/36
(52) U.S. Cl. .................... 623/23.61; 523/115; 424/423; 128/898
(58) Field of Search ........................... 623/23.61, 23.62, 623/23.56; 128/898; 501/1; 423/308, 309, 311; 424/422, 423, 549; 514/785, 801, 802; 523/115

(56) References Cited

U.S. PATENT DOCUMENTS

| | | | | |
|---|---|---|---|---|
| 3,892,648 A | * | 7/1975 | Phillips et al. ......... 128/DIG. 8 |
| 4,373,217 A | * | 2/1983 | Draenert ........................... 3/1.9 |
| 4,861,733 A | * | 8/1989 | White .............................. 501/1 |
| 4,917,702 A | * | 4/1990 | Scheicher et al. ............. 623/16 |
| 5,023,090 A | * | 6/1991 | Levin ........................... 424/520 |
| 5,053,212 A | * | 10/1991 | Constantz et al. ........... 423/305 |
| 5,073,373 A | * | 12/1991 | O'Leary et al. ............. 424/422 |
| 5,425,770 A | * | 6/1995 | Piez et al. ..................... 623/16 |
| 5,522,896 A | * | 6/1996 | Prescott ........................ 623/16 |
| 5,837,752 A | * | 11/1998 | Shastri et al. ................ 424/423 |
| 6,020,396 A | * | 2/2000 | Jacobs ......................... 523/116 |

* cited by examiner

*Primary Examiner*—Corrine McDermott
*Assistant Examiner*—Urmi Chattopadhyay
(74) *Attorney, Agent, or Firm*—Christie, Parker & Hale, LLP

(57) ABSTRACT

Methods for correcting defects at bone repair sites are provided, which use a moldable, post-implantable bone conforming material. The method includes the steps of preparing a bone conforming material, shaping the moldable paste, curing the paste to form a hardened implant, disposing the implant at a repair site, allowing tissue to overlay the repair site during healing and if necessary, further molding the implant to the desired contours of the bony structure being repaired for up to eight weeks after the surgery by applying pressure to the tissue overlaying the implant.

44 Claims, No Drawings

MOLDABLE POST-IMPLANTATION BONE FILLER AND METHOD

CROSS-REFERENCE TO RELATED APPLICATION

This patent application is based on and claims priority of U.S. Provisional Patent Application Ser. No. 60/126,745 filed on Mar. 29, 1999, which is incorporated by reference herein.

FIELD OF THE INVENTION

The invention relates to the field of biocompatible bone fillers and bone conforming materials, and more particularly to a bone filler and bone conforming agent that can be shaped into an implant that remains moldable for some time after being implanted in the body, and a method for using same.

BACKGROUND OF THE INVENTION

The invention is directed to moldable, post-implantation bone fillers and bone conforming materials that can be formed into an implant that remains moldable for some time after being implanted in the body and a method for using the same. During various surgical procedures, including but not limited to orthognathic surgeries (surgeries of the jaw and related areas), the surgeon will often identify depressions and other deformities in the shape and contour of various bone structures. Indeed, in the field of facial surgeries, one common reason to carry out surgical procedures is to make aesthetic and/or functional improvements to the face. Many times these surgeries require changing the size, shape, and/or position of underlying bone structure (e.g. shortening, lengthening, or widening the jaw, augmenting the chin, etc). Because the underlying bone structure of interest (which is covered with muscle, fat, skin and other tissues) has a great influence in determining the exterior contours and appearance of the body, the ability to easily correct defects and deficiencies in the post-operative bone structure would be very helpful.

Presently, there are several methods surgeons employ to accomplish this, including using implants made of silicone, various metals (such as stainless steel and other materials), hydroxyapatite and other material. There are sometimes infection problems associated with implants made of materials that are not completely biocompatible, such as silicone implants. Hydroxyapatite, $Ca_{10}(PO_4)_6(OH)_2$, is similar in property to coral, which is remarkably close in chemical composition and structure to human bone. In fact, human bone will grow in to the porous structure of the implant material and can sometimes even entirely replace the implanted hydroxyapatite. Other common implant materials include highly processed bone (from animal or cadaver sources, U.S. Pat. No. 5,501,706), calcium phosphate cements (U.S. Pat. No. 5,697,981), physiological serums containing hydroxyapatite (U.S. Pat. No. 5,591,232) and sintered apatite bodies and composites (U.S. Pat. No. 4,503,157).

Hydroxyapatite is typically provided in the form of microspherical particles that can be implanted to a site that needs augmentation, for example, by injection via a syringe-like device. Since the microspheres are like small ball bearings, they tend to drift, move or "flow" away from the implantation site after being implanted. Thus, little control can be exercised over the results. Eventually, the hydroxyapatite microspheres will stabilize (although as explained above, not always where the surgeon wants them to be concentrated). In other cases, hydroxyapatite is provided in solid blocks that can be machined in to a particular shape, and then inserted in the desired location adjacent to the bone undergoing repair, replacement or modification. The solid block sources must be shaped to fit the specific requirements of the repaired, replaced or modified bone and are not easily fabricated to conform to the desired bone shape. Typically, such solid blocks of pure hydroxyapatite are appropriate for use in expanding jaws and the like where a solid structure without any moldability is desired.

While calcium phosphate cements are known that harden in-situ or that harden and then are shaped in to a pre-formed object useful in bone repair, there remains a need for a moldable, post-implantable bone filler and bone conforming material and a method for using such a bone filler and bone conforming material.

SUMMARY OF THE INVENTION

The invention provides a moldable, post-implantable bone conforming material and a method for using the bone filler. The bone conforming material comprises an apatite material and a fibrous material, such as fibrous proteins (e.g. collagen) mixed with enough physiological fluid added to form a paste. The bone filler and the method of using the bone material permits a surgeon to form implants of desired shapes and sizes outside of the body, implant the bone conforming material against the bone, close the surgical site, and continue to be able to adjust or modify the contours of the patient body in the areas with the bone conforming material for a period of time by applying pressure to the skin, muscle, and other tissue overlaying the bone conforming material implant to thereby mold or shape the implanted bone conforming material. The time period during which the bone conforming material can continue to be molded is about eight weeks or longer.

There are tremendous advantages to the bone conforming material of the present invention. First, a surgeon can mix together a moldable bone conforming material and pre-shape the bone conforming material into a desired shape prior to implantation. The surgeon will then dry the molded bone conforming material, thereby curing it to a hardened shape and state, preferably by placing it under a heat lamp, in a heated oven, in a dehydration unit under warm/hot air flow or a dessicant, or by other suitable curing means. In its hardened state, it retains its shape and state. It is also possible to rely on air drying solely, which takes considerably more time, as compared to drying using a heating unit. After the hardened implant is positioned in a desired place in the body against a bone structure, it becomes saturated with blood and other physiological fluids and softens somewhat like a hardened sponge softens when saturated. In its softened state, it can be molded further at the implantation site to more closely conform to the bone and continue being shaped as required. However, even when it is saturated and softens, it will not crumble or break up, and remains moldable. After the surgery, the surgeon will close the surgery site over the implant. The surgical site will remain inflamed and swollen for some time, generally for at least several days to several weeks. For this reason, it is not always apparent to the doctor at the time of implantation how best to shape the bone conforming material to the bone. The ability to mold the bone conforming material, after the swelling has gone down, allows the surgeon to carry out further shaping of the bone conforming material to achieve improved aesthetic results. In addition, pre-curing the bone conforming material prevents the inherent drift of bone material associated with microspherical bone conforming material materials and methods.

DETAILED DESCRIPTION OF THE INVENTION

The bone conforming material of the present invention comprises an apatite, such as hydroxyapatite and a fibrous protein (e.g. collagen) with enough of a physiological fluid (e.g. saline solution) added to form a paste. The inventor has successfully used a source of porous hydroxyapatite, known as INTERPORE 200® from Nobel Biocare USA, of Yorba Linda, Calif. INTERPORE 200® comprises hydroxyapatite granules that range, in nominal diameter, from about 425 to 1000 microns. Other satisfactory apatitic materials for the purposes of the present invention would include cortical bone powder, acidic or neutralized calcium phosphates, apatitic cements formed by neutralizing acidic calcium phosphates, bone powder from human or animal cadavers, powdered coral, fluoroapatite, carbonate apatite, chloroapatite, physiological bone serum and mixtures thereof. The inventor has incorporated a source of fibrous proteins in the form of collagen, known as AVITENE® microfibrillar collagen (offered by C.R. Bard, Inc., of Woburn, Mass.). AVITENE® microfibrillar collagen (hereinafter referred to simply as "AVITENE®") is sold for use as a 100% active form of collagen (derived from cowhide) hemostate that potentiates the body's natural clotting mechanism and helps prevent post-operative bleeding. One contraindication of AVITENE® is that since it fills porosities of cancellous bone, the AVITENE® should not be used in areas where methylmethacrylate adhesives are to be used. Other satisfactory fibrous materials for purposes of the present invention would include collagen fibrils (Type I–III), fibrin, gelatin, fibrolamellar bone, cartilage, polysaccharide elastomers, natural rubber and mixtures thereof.

In the present invention, the inventor uses AVITENE® as a binding agent to hold together and give shape and form to the hydroxyapatite when mixed together with the physiological fluid to thereby prevent it from dissolving and melting out of the implantation site. Hydroxyapatite and AVITENE® microfibrillar collagen are mixed with a saline solution, for example, to afford a paste or clay-like moldable mixture that remains moldable for an extended time period, yet retains its shape before complete hardening. Other suitable physiological fluids for purposes of the invention would include any physiologically buffered solutions, namely sodium citrate, phosphate buffers such as TRIS, Polymixin B sulfate, sterile water, Bacitracin or any other suitable antimicrobial agents, blood serum, blood plasma and mixtures thereof. For biocompatability, the inventor has used saline to moisten the mixture of hydroxyapatite and AVITENE®, but purified water or physiological fluids could also probably be used as well. Although in the preferred embodiment, hydroxyapatite is used with AVITENE®, other apatitic materials might be used in lieu of hydroxyapatite and other fibrous proteins or other materials might be used to replace the AVITENE®.

The paste or clay is shaped into a desired implant configuration (such as a sphere, a boule, a tennis racket, flattened ovals, a paddle, etc.), and is placed under a heat lamp to drive away excess liquid and cure the implant. The inventor has used a 65 watt heat lamp placed close to the shaped implant. Other methods can be used to drive away excess moisture and cure the mixture, such as placing the shaped mixture in a heated vacuum chamber, drying oven, or other suitable drying means. In attempts to eliminate the step of first hardening the molded implant before it is implanted into the body, the results were not as optimal. The unhardened implant, when infused with blood, became very soggy and would not hold a desired shape. When the surgical site was closed, the pressure of the tissue would tend to flatten out the implant. When dried, the implant is basically a mineralized solid, yet retains microscopic pores. The implant is then placed at the surgery site on the bone where a defect is to be corrected and/or the bone is to be augmented. Since the surgical site is seldom completely dry and free from bodily fluids (namely blood and lymphatic fluid), the implant will absorb blood and other physiological fluids, and once more become pliable, much as a dry sponge becomes pliable when moistened. If the site is too dry, the surgeon can allow blood and other bodily fluids to infuse the surgical site. However, even when it is saturated and softens, the implant will resist crumbling and will break up, and remains moldable. The surgeon can then further mold the implant to better fit the implant against the bone and as required for the particular application. For example, cheek bones can be made as described above, and can be further shaped and conformed once placed against the bone. The implant will adhere to the bone very well, and will resist slippage and movement, yet can be molded by the application of direct pressure to it to conform exactly to the bone.

After the surgery is complete, the surgical site will be closed using standard surgical procedures, and healing in the overlaying tissue will begin to take place. Once the swelling has diminished, the doctor can, by applying pressure to the site, continue to mold the bone conforming material and influence the perceived shape of the underlying bony and implant structure. For example, if the augmented cheek bone is too angular or pronounced, the surgeon can flatten or round it as desired. Thus, by making adjustments to the underlying implant and bony structure, the doctor has the opportunity to make fine adjustments to contours of the overlying soft tissue. During this period, the patient must avoid pressure applied to the part of the body with the bone conforming material (i.e. the patient must sleep on a soft pillow and avoid contact sports). As stated above, after about eight weeks, the bone conforming material will become fully cured and the shaped implant becomes completely hardened, after which time it will no longer be capable of being molded further. The inventor anticipates that the curing time might be varied by changing the materials used in the implant. Eventually, bone will grow into the porous structure of the implanted bone conforming material through bone remodeling processes, then with time partially or completely replace the bone conforming material.

EXAMPLE 1

Forming the Implant Material

Five cc (5.4 gm) of INTERPORE 200® porous hydroxyapatite is placed in a dry plastic bowl. Five cc of a sodium chloride solution (0.9% sodium chloride in distilled water) are added (optionally including Polymyxin B Sulfate—500,000 units and Bacitracian—50,000 units, or other known antimicrobial agents to control possible infection). The mixture is stirred until all of the hydroxyapatite is moistened to form a paste. Small amounts of AVITENE® are added to the moistened hydroxyapatite, with complete mixing after each addition. A sufficient amount of AVITENE® is added until the mixture will hold together (usually about 1.0 gm depending upon room temperature and humidity) and subsequently is formed and shaped to the desired implant shape depending on the requirements.

The shaped mixture is then placed under a lamp (e.g. a 65 watt heat goose neck lamp placed about 3 to 4 inches away from the shaped mixture) for between 15 minutes and 1.5 hours, or until the shaped mixture is hardened. The hardening or curing time varies depending upon the size and the shape of the implant being dried and hardened and the distance between the shaped implant and the lamp. In practice, heating the mixture longer than 1.5 hours does not harm the mixture. To increase the drying and hardening time, the lamp can be brought closer to the shaped implant.

EXAMPLE 2

Implanting the Hardened Implant

After the implant is hardened and cooled down, the surgeon places it against exposed bone. For example, for cheek bone augmentation, the hardened implant will be placed in the vicinity of the deficient prominence of the cheek bone with the overlying tissue removed to expose the bone. The hardened implant will almost immediately soak up blood and lymphatic fluids. When moistened with bodily fluids, the implant will once more become pliable, and can be shaped further to closely conform to the bony structure and/or to assume the desired shape (e.g. cheek bone contour). Although the moistened implant becomes pliable and moldable, unlike plain hydroxyapatite particles, which tend to disperse from the implantation site (since nothing keeps them in place), the implant of the invention will remain in place and retain its shape absent pressure being applied to the implant. Presently available solid preformed blocks of pure hydroxyapatite are not moldable at all even when moistened, and once implanted, the surgeon cannot make fine, post-operative adjustments. As noted above, even when the implant is saturated and becomes softened, it will not crumble or break up, and remains moldable. Furthermore, since the material of the implant closely adheres to the bone, unlike implants constructed of silicone and other materials, the implant does not need to be mechanically attached with sutures, staples, screws, or otherwise.

EXAMPLE 3

Post Implantation Molding of the Implant

After the surgical site is closed and swelling has receded, the implant remains moldable for about eight weeks or longer, after which time the implant will be become completely cured and will no longer be moldable. Prior to becoming completely cured, the surgeon can continue to affect changes to the shape of the implant by applying mechanical pressure to tissue in the vicinity of (e.g. overlaying) the implant to shape it further. Since the implant will retain its shape absent pressure being applied, changes to the shape of the implant will impart changes to the overall appearance contours of the soft tissue overlying and in the vicinity of the implant. Eventually, bone and/or connective tissue (e.g., in the form of osteoblasts) will grow into the implant. After a time, the implant will be partially or completely replaced with bone tissue, without changing the overall size and shape of the implant.

The foregoing description is not intended to represent the only form of the invention in regard to the details of this construction and manner of operation. In fact, it will be evidence to one skilled in the art that modifications and variations may be made without departing from the spirit and scope of the invention. Although specific terms have been employed, they are intended in a general and descriptive sense only and not for the purpose of limitation.

What is claimed is:

1. A moldable bone conforming material which remains moldable after being implanted for a period of time, comprising:
   at least one apatitic material;
   at least one fibrous material comprising microfibrillar collagen; and
   at least one fluid;
   wherein the at least one apatitic material, the at least one fibrous material and the at least one fluid when mixed together form a moldable paste which is shaped and cured outside of subject's body into an implant of a desired size and shape and which is then implanted at a bone repair site, wherein the implant is reshapeable at a post-operative bone repair site to achieve an aesthetic shape in a subject.

2. The moldable bone conforming material according to claim 1, wherein the apatitic material is in the form of a porous solid or granular particles.

3. The moldable bone conforming material according to claim 1, wherein the apatitic material is selected from the group consisting of hydroxyapatite, apatitic cements, cortical bone from human or animal cadavers, coral, acidic calcium phosphates, neutral calcium phosphates, fluoroapatite, carbonate apatite, chloroapatite, physiological bone serum and mixtures thereof.

4. The moldable bone conforming material according to claim 1, wherein the apatitic material is hydroxyapatite granules ranging in diameter from 425 to 1000 microns.

5. The moldable bone conforming material according to claim 1, wherein the fluid is a physiological buffer solution of sodium chloride.

6. The moldable bone conforming material according to claim 1, wherein the fluid contains antimicrobial agents.

7. The moldable bone conforming material according to claim 1, wherein the fluid contains a mixture of Polymixin B sulfate and Bacitracin.

8. The moldable bone conforming material according to claim 1, wherein the fluid is selected from the group consisting of a solution of sodium chloride, sodium citrate, Polymixin B sulfate, Bacitracin, sterile water, blood serum and mixtures thereof.

9. The moldable bone conforming material according to claim 1, wherein the apatitic material is hydroxyapatite granules ranging in diameter from 425 to 1000 microns and the physiological fluid is a mixture of sodium chloride solution, Polymixin B sulfate and Bacitracin.

10. A moldable bone conforming material which remains moldable after being implanted for a period of time, comprising:
    at least one apatitic material;
    at least one fibrous material comprising microfibrillar collagen; and
    at least one fluid;
    wherein the at least one apatitic material, the at least one fibrous material and the at least one fluid when mixed together form a moldable paste, which moldable paste when formed into an implant configuration is then cured to a hardened state to form a cured implant, which cured implant is suitable for implantation at a bone repair site, and which is reshapeable at a post-operative bone repair site to achieve an aesthetic shape in a subject.

11. The moldable bone conforming material according to claim 10, wherein the apatitic material is selected from the group consisting of hydroxyapatite, apatitic cements, cortical bone from human or animal cadavers, coral, acidic calcium phosphates, neutral calcium phosphates, fluoroapatite, carbonate apatite, chloroapatite, physiological bone serum and mixtures thereof.

12. The moldable bone conforming material according to claim 10, wherein the apatitic material is hydroxyapatite granules ranging in diameter from 425 to 1000 microns.

13. The moldable bone conforming material according to claim 10, wherein the fluid is a physiological buffer solution of sodium chloride.

14. The moldable bone conforming material according to claim 10, further including antimicrobial agents.

15. The moldable bone conforming material according to claim 10, wherein curing is affected by at least one of placing the shaped implant under a heat lamp, in a heated oven, in a dehydration unit, and in a dessicant.

16. A moldable bone conforming material which remains moldable after being implanted for a period of time, comprising:
   at least one apatitic material comprising hydroxyapatite granules ranging in diameter from 425 to 1000 microns;
   at least one fibrous material; and
   at least one fluid containing a mixture of Polymixin B sulfate and Bacitracin;
   wherein the at least one apatitic material, the at least one fibrous material and the at least one fluid are mixed together to form a moldable paste suitable for implantation at a bone repair site, wherein the moldable paste is capable of being shaped and cured outside of a subject's body into an implant of a desired size and shape, wherein the cured implant is remoldable at a post-operative bone repair site to achieve an aesthetic shape in a subject.

17. The moldable bone conforming material according to claim 16, wherein the fibrous material is in the form of collagen.

18. The moldable bone conforming material according to claim 16, wherein the fibrous material is selected from the group consisting of microfibrillar collagen, collagen fibrils, fibrin, gelatin, polysaccharide elastomers, natural rubber, fibrolamellar bone, cartilage and mixtures thereof.

19. The moldable bone conforming material according to claim 16, wherein the fluid further comprises a physiological buffer solution of sodium chloride.

20. The moldable bone conforming material according to claim 16, wherein the cured moldable paste, once implanted, can be shaped or reshaped, if necessary, at the post-operative bone repair site to achieve an aesthetic shape in a subject.

21. A method for correcting bone deficiencies at a bone repair site, comprising:
   preparing a bone conforming material which consists essentially of at least one apatitic material, at least one fibrous material, and a fluid, which when mixed together form a moldable paste;
   shaping the paste to form a desired implant configuration;
   curing the implant configuration to sufficiently harden the implant configuration;
   disposing the implant configuration at the bone repair site wherein it will absorb bodily fluid and become softened;
   molding the implant configuration further if necessary to conform the implant configuration to the bone repair site;
   closing the bone repair site, and
   remolding the implant configuration, after the bone repair site is closed, by applying pressure to the tissue overlaying the implant configuration to thereby affect reshaping of the implant configuration.

22. The method according to claim 21, wherein the step of remolding of the implant configuration can be carried out after any swelling and inflammation in the vicinity of the bone repair site has diminished.

23. The method according to claim 21, wherein the step of remolding the implant configuration can be carried out for approximately eight weeks.

24. The method according to claim 21, wherein bodily tissue will grow into the implant configuration during healing and eventually replace the implant configuration with tissue.

25. The method according to claim 21, wherein the apatitic material is in the form of a porous solid or granular particles.

26. The method according to claim 25, wherein the granular particles are microspherical particles.

27. The method according to claim 21, wherein the apatitic material is selected from the group consisting of at least one of hydroxyapatite, apatitic cements, cortical bone from human or animal cadavers, coral, acidic calcium phosphates, neutral calcium phosphates, fluoroapatite, carbonate apatite, chloroapatite, physiological bone serum and mixtures thereof.

28. The method according to claim 21, wherein the apatitic material is hydroxyapatite granules ranging in diameter from 425 to 1000 microns.

29. The method according to claim 21, wherein the fibrous material is in the form of collagen.

30. The method according to claim 21, wherein the fibrous material is selected from by the group consisting of at least one of microfibrillar collagen, collagen fibrils, fibrin, gelatin, polysaccharide elastomers, natural rubber, fibrolamellar bone, cartilage and mixtures thereof.

31. The method according to claim 21, wherein the fibrous material is microfibrillar collagen.

32. The method according to claim 21, wherein the fluid is a physiological buffer solution of sodium chloride.

33. The method according to claim 21, wherein the fluid contains antimicrobial agents.

34. The method according to claim 33, wherein the antimicrobial agents comprise a mixture of Polymixin B sulfate and Bacitracin.

35. The method according to claim 21, wherein the fluid is selected from the group consisting of a solution of at least one of sodium chloride, sodium citrate, Polymixin B sulfate, Bacitracin, in water, blood serum and mixtures thereof.

36. The method according to claim 21, wherein the curing step comprises at least one of placing the shaped implant under a heat lamp, in a heated oven, in a dehydration unit, under warm/hot air flow, and in a dessicant.

37. The method according to claim 21, wherein the curing step comprises placing the shaped implant under a heat lamp until the implant hardens.

38. The method according to claim 21, for use in maxillofacial surgery and facial reconstruction surgery.

39. A method of surgery which permits post-operative reshaping of an implant at a bone repair site, comprising:
   exposing a site for bone repair;
   preparing a bone conforming material which consists essentially of at least one apatitic material, at least one fibrous material, and a fluid, which when mixed together form a moldable paste;
   shaping the paste to form a desired implant configuration;

curing the implant configuration to sufficiently harden the implant configuration;

disposing the implant configuration at the bone repair site;

molding the implant configuration, if necessary, to conform to correct a bone defect or restore a shape to a bone at the bone repair site;

closing the bone repair site; and remolding the implant after the surgery, if necessary, by applying pressure to the overlaying tissue to modify the shape of the implant configuration, wherein the step of remolding the implant configuration after the surgery can be accomplished without the need for anesthetics and can be carried out for approximately eight weeks after the surgery.

40. The surgical method according to claim 39, wherein the curing step comprises at least one of placing the implant configuration under a heat lamp, in a heated oven, in a dehydration unit, under warm/hot air flow, and in a dessicant.

41. The surgical method according to claim 39, wherein the curing step comprises placing the implant configuration under a heat lamp until the implant hardens.

42. The method of surgery according to claim 39, wherein the bone repair site and body member upon which the surgery is performed is the face.

43. The method of surgery according to claim 39, wherein the bone repair site and body member upon which the surgery performed is the cheekbone.

44. A method for correcting defects in a bony structure comprising:

preparing a bone conforming material which consists essentially of at least one apatitic material, at least one fibrous material, and a fluid, which when mixed together form a moldable paste;

shaping the paste to form an implant having a desired shape;

curing the implant to sufficiently harden the implant;

placing the implant at a bone repair site;

molding the implant, if necessary, to correct the bone defect at the bone repair site;

closing the bone repair site;

allowing tissue to grow into and overlay the bone repair site during healing; and remolding the implant, if necessary, by applying direct pressure to the overlaying tissue to modify the shape of the implant, wherein the step of remolding the implant can be accomplished without the need for anesthetics and can be carried out for approximately eight weeks after application to the bone repair site.

* * * * *

UNITED STATES PATENT AND TRADEMARK OFFICE
CERTIFICATE OF CORRECTION

PATENT NO.     : 6,506,217 B1
DATED          : January 14, 2003
INVENTOR(S)    : G. William Arnett It is certified that error appears in the above-identified patent and that said Letters Patent is hereby corrected as shown below:

<u>Column 6,</u>
Line 11, replace "when" with -- are --
Line 12, insert -- to -- after "together" and insert -- capable of being -- after "is"
Line 13, insert -- a -- after "of"
Line 14, delete "and which is then implanted" and replace with -- for implanting --
Line 15, insert -- cured -- before "implant" and replace "reshapeable" with
-- remoldable --
Line 57, replace "when" with -- are --
Line 58, insert -- to -- after "together"
Line 59, replace "when" with -- is capable of being -- and replace "is then"
with -- and --
Line 62, replace "reshapeable" with -- remoldable --

Signed and Sealed this

Twenty-sixth Day of August, 2003

JAMES E. ROGAN
*Director of the United States Patent and Trademark Office*